United States Patent
Swaminathan

(10) Patent No.: US 6,517,533 B1
(45) Date of Patent: *Feb. 11, 2003

(54) BALLOON CATHETER FOR CONTROLLING TISSUE REMODELING AND/OR TISSUE PROLIFERATION

(76) Inventor: M. J. Swaminathan, 3415 Misty Meadow Dr., Dallas, TX (US) 75287

(*) Notice: Subject to any disclaimer, the term of this patent is extended or adjusted under 35 U.S.C. 154(b) by 0 days.

This patent is subject to a terminal disclaimer.

(21) Appl. No.: 09/305,137

(22) Filed: May 4, 1999

Related U.S. Application Data

(63) Continuation-in-part of application No. 08/902,020, filed on Jul. 29, 1997, now Pat. No. 5,902,299.

(51) Int. Cl.[7] .............................................. A61B 18/18
(52) U.S. Cl. .......................... 606/20; 606/21; 606/23; 600/3
(58) Field of Search ............................. 606/20, 21, 22, 606/23–26; 600/1, 2, 3

(56) References Cited

U.S. PATENT DOCUMENTS

| | | | |
|---|---|---|---|
| 4,292,976 A | | 10/1981 | Banka |
| 4,512,762 A | * | 4/1985 | Spears ........................ 604/21 |
| 5,106,360 A | * | 4/1992 | Ishiwara et al. .............. 600/2 |
| 5,108,390 A | | 4/1992 | Potocky et al. |
| 5,135,484 A | | 8/1992 | Wright |
| 5,213,561 A | * | 5/1993 | Weinstein et al. ............. 600/7 |
| 5,334,181 A | | 8/1994 | Rubinsky et al. |
| 5,411,466 A | * | 5/1995 | Hess ............................ 600/3 |
| 5,417,653 A | * | 5/1995 | Sahota et al. ................ 604/20 |
| 5,419,760 A | * | 5/1995 | Narciso, Jr. .................. 604/8 |
| 5,447,497 A | * | 9/1995 | Sogars et al. ............... 604/101 |
| 5,452,582 A | | 9/1995 | Longsworth |
| 5,575,811 A | | 11/1996 | Reid et al. |
| 5,616,114 A | * | 4/1997 | Thornton et al. .............. 600/3 |
| 5,624,392 A | | 4/1997 | Saab |
| 5,674,198 A | | 10/1997 | Leone |
| 5,741,248 A | | 4/1998 | Stern et al. |
| 5,868,735 A | | 2/1999 | Lafontaine |
| 5,947,889 A | * | 9/1999 | Hehrlein ....................... 600/3 |
| 5,957,917 A | | 9/1999 | Doiron et al. |
| 5,964,751 A | | 10/1999 | Amplatz et al. |
| 5,971,909 A | | 10/1999 | Bradshaw et al. |
| 5,971,979 A | | 10/1999 | Joye et al. |
| 5,993,374 A | * | 11/1999 | Kick ............................ 600/8 |
| 6,010,445 A | | 1/2000 | Armini et al. |
| 6,013,053 A | | 1/2000 | Bower et al. |
| 6,074,338 A | * | 6/2000 | Popowski et al. ............. 600/3 |
| 6,099,499 A | | 8/2000 | Ciamacco, Jr. |
| 6,102,905 A | | 8/2000 | Baxter et al. |
| 6,110,168 A | | 8/2000 | Ginsburg |
| 6,117,064 A | | 9/2000 | Apple et al. |
| 6,355,029 B1 | | 3/2002 | Joye et al. |

* cited by examiner

*Primary Examiner*—Linda C. M. Dvorak
*Assistant Examiner*—Roy Gibson
(74) *Attorney, Agent, or Firm*—Pennie & Edmonds LLP

(57) ABSTRACT

The invention relates to a catheter and method for controlling tissue remodeling or proliferation. The catheter includes an outer balloon located on a distal end of the catheter, a first lumen in fluid communication with the outer balloon and fluidly connected to a source of liquid for expanding the outer balloon with liquid to contact the tissue site, and a second lumen fluidly connected to a source of coolant fluid at a proximal end for transporting the coolant fluid to a distal end of the second lumen to cool the liquid in the outer balloon and thereby the tissue site to a cryo-therapeutic temperature. The second lumen includes an orifice configured and dimensioned to allow the coolant fluid to expand as it passes therethrough to reduce coolant fluid temperature. In another embodiment, the outer balloon is coated or expanded with a media. The media is normally in an inactive state in which it has no effect on tissue, and is transformable upon addition of energy to an active state in which the media affects tissue remodeling or proliferation. An activation factor for providing the energy needed to transform the media to the active state is introduced through the inner balloon.

19 Claims, 5 Drawing Sheets

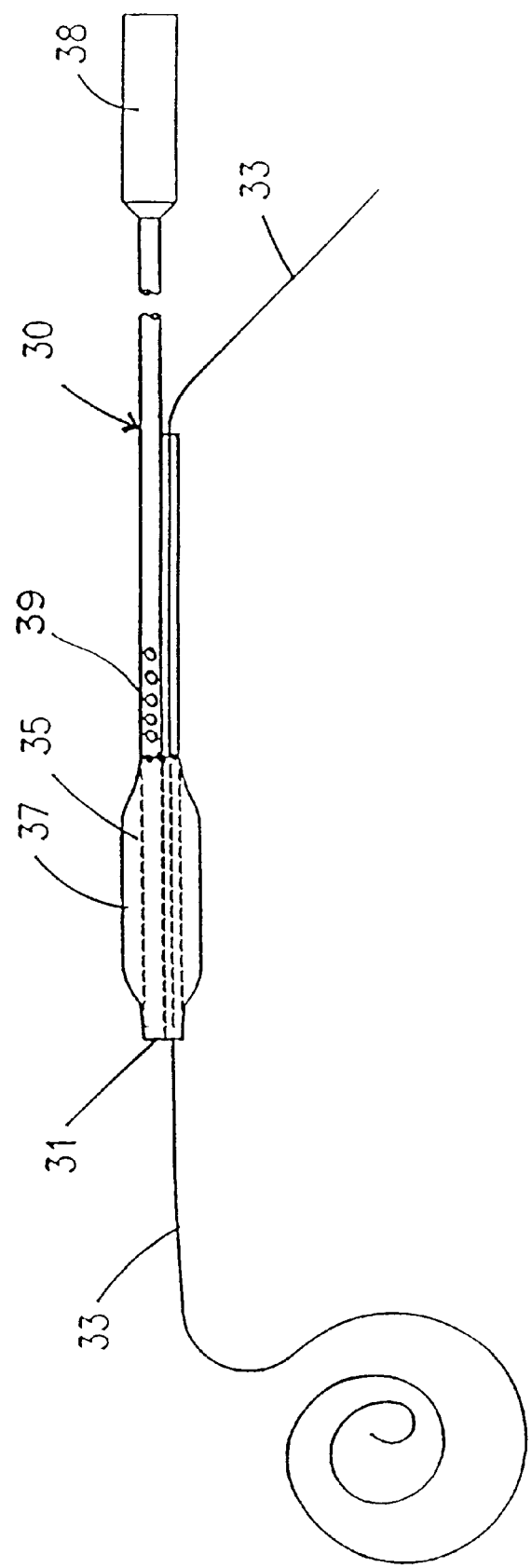

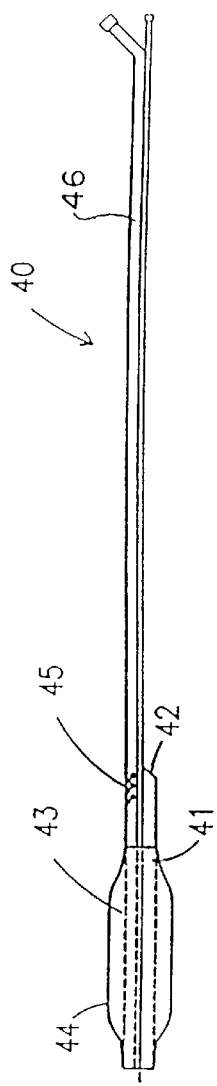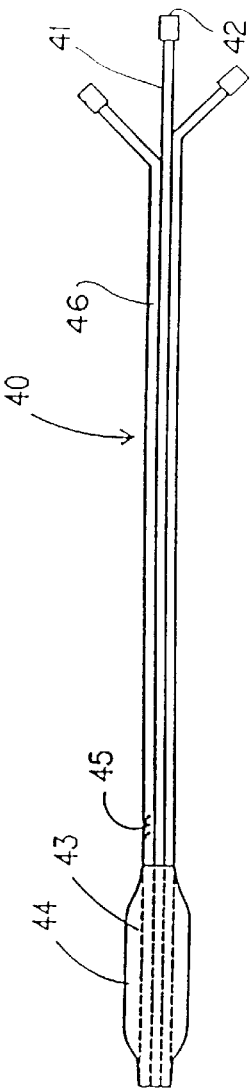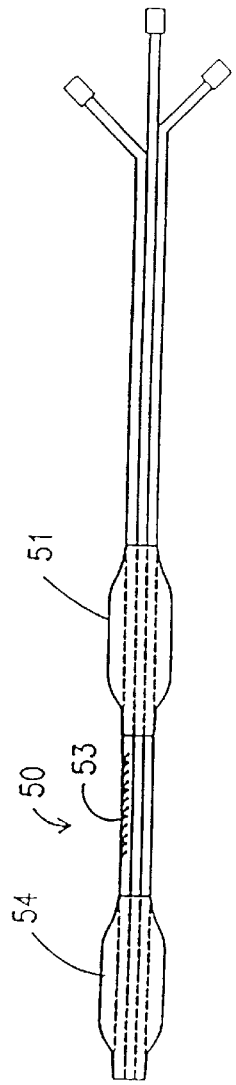

BALLOON CATHETER FOR CONTROLLING TISSUE REMODELING AND/OR TISSUE PROLIFERATION

CROSS-REFERENCE TO RELATED APPLICATIONS

This is a continuation-in-part of U.S. Ser. No. 08/902,020, filed Jul. 29, 1997, now U.S. Pat. No. 5,902,299.

FIELD OF THE INVENTION

The present invention relates to a device and method for controlling or eliminating tissue remodeling or proliferation, and in particular to a balloon catheter for controlling or eliminating tissue remodeling or proliferation.

BACKGROUND OF THE INVENTION

Cryotherapy, the therapeutic use of cold, is known in the medical field. Some of the well defined applications of cryotherapy include the following:

(1) Tissues collected from bovine, pigs, or sheep are preserved at reduced temperature so that the elastic membrane or elastin present in the tissues is protected for subsequent applications. Without the use of such temperature reduction, the tissues dry out and lose their original mechanical, physical and chemical properties.

(2) During open heart surgery, when the heart is opened to either replace a valve or an underlying diseased coronary artery, the myocardium or the tissues surrounding the heart are exposed to reduced temperature by dipping them in ice or sub-cooled water while the surgery is underway to preserve them.

(3) During open heart surgery, when the aorta is cross-clamped and blood from the heart is directed into a heart-lung machine, the blood is mixed with cold cardioplegia solution to preserve the cells and other essential components in the blood, an especially critical procedure when the surgery is lengthy.

(4) Bovine and other homograft valves that have been preserved in cryo-based solutions and reduced temperature environment have been shown to have superior performance during long term follow-up studies when compared with mechanical bileaflet or single leaflet valves.

(5) In many pain management therapeutic situations, the area or region of acute pain is exposed to reduced temperature fluids or "cold packs" to reduce nerve damage and relieve pain.

(6) External probes have been used in the treatment of endometrial ablation and for prostate treatment. These probes are connected to a cryogenerator and the probe tips are used to treat the tissues in the open areas of the body.

(7) Treating arrhythmia with exterior probes has been described in various situations. When the chest is opened during bypass surgery, sudden arrythmias situations have been treated by putting cold probes on the myocardial tissue to restore cardiac flow. These applications are currently done using intra-cardiac catheters to spot the areas of myocardial viability and to target the cryo-probes to the unviable zones. These are usually non-balloon cryo-applications.

The present invention is directed to the use of cryotherapy for reducing tissue injury after balloon angioplasty or stent implantation. One of the most common causes of failure of angioplasty or stent implantation is restenosis. Restenosis is evidenced when the artery re-occludes due to tissue ingrowth and/or elastic recoil of the arterial wall at the site of the prior occlusion. After a balloon angioplasty procedure or stent implantation procedure has been completed, the arterial wall often exhibits damage or inflammation due to the required use of force from inflation of a balloon catheter against the cellular layers of the arterial wall. Specifically, when a balloon is inflated at the site of a lesion where the artery is occluded, the lesion is mechanically pushed up by force acting thereon due to inflation of the balloon. Pathology of experiments in pigs and sheep reveals that the balloon inflation causes endothelial injury as well as tissue dislodgement at the site of the lesion. Such an injury is characterized by inner lumen wall cracks that are filled up with blood and some thrombus (clotting material). These cracks may infiltrate into the second and third layers of the vessel wall that are termed adventitia and media primarily composed of collagen, smooth muscle cells and elastic cells that contribute to the compliance of the artery.

When these layers are disrupted due to balloon inflation or stent implantation, compliance response is lost. This results in proliferation of cells as a function of time. Although the proliferation starts immediately after the injury to the arterial wall, maximum proliferation may be observed 6 to 18 months after the initial injury.

The present invention is also directed to a device and method for using cryotherapy in any clinical situation in which the modeling or proliferation of tissue needs to be controlled or eliminated. These clinical situations may be vascular or non-vascular applications, and may include coronary or non-coronary applications. For example, the device and method according to the present invention can be used to treat cancer by terminating angiogenesis, i.e the formation of a network of capillaries and veins around or inside a cancerous tumor.

In addition to the use of temperature, other forms of energy such as light or radiation can be used to control or eliminate tissue remodeling or proliferation. In photodynamic therapy, light is combined with a photosensitive drug. In this regard, the present invention is also directed to a balloon catheter for photodynamic therapy or radiation delivery.

SUMMARY OF THE INVENTION

The present invention relates to a catheter for controlling tissue remodeling or proliferation at a tissue site. The catheter includes an outer balloon located on a distal end of the catheter, a first lumen in fluid communication with the outer balloon and fluidly connected to a source of liquid for expanding the outer balloon with liquid to contact the tissue site, and a second lumen fluidly connected to a source of coolant fluid at a proximal end for transporting the coolant fluid to a distal end of the second lumen to cool the liquid in the outer balloon and thereby the tissue site to a cryotherapeutic temperature. In a preferred embodiment, the coolant fluid temperature is sufficient to freeze the liquid after expansion through the orifice. The second lumen includes an orifice configured and dimensioned to allow the coolant fluid to expand as it passes therethrough to reduce coolant fluid temperature.

Preferably, the outer balloon has a temperature sensor for monitoring the temperature of the tissue site and there is a valve between the fluid coolant source and the second lumen for controlling introduction of the coolant gas into the second lumen.

The catheter may include an inner balloon in fluid communication with the distal end of the second lumen in close proximity to the outer balloon. The fluid communication between the second lumen and the inner balloon is through the orifice to allow the coolant fluid to expand into the inner balloon. The catheter may also include a third lumen configured and dimensioned to receive a guide wire for directing the catheter to the tissue site.

In order to facilitate removal of coolant fluid from the inner balloon, the catheter may have a fourth lumen in fluid communication with the inner balloon at a distal end. This fourth lumen may be fluidly connected to a vacuum to assist in removing the coolant fluid from the inner balloon.

In another embodiment, the catheter has a first lumen configured and dimensioned to receive a guide wire for directing the catheter to the tissue site, an outer balloon located on a distal end of the catheter, a second lumen in fluid communication with the outer balloon at a distal end and fluidly connected to a source of a media at a proximal end for expanding the outer balloon with the media so that the outer balloon is in contact with the tissue site. The media is normally in an inactive state in which the media has no effect on tissue remodeling or proliferation, but can be transformed to an active state upon addition of energy in which the media effects tissue remodeling or proliferation. The catheter also includes an inner balloon located on the distal end of the catheter and in close proximity to the outer balloon and a third lumen in fluid communication with the inner balloon at a distal end and fluidly connected to a source of an activation factor at a proximal end for transporting the activation factor to the inner balloon to provide the energy needed to transform the media to the active state.

The activation factor may be light, heat, or some other form of energy. Preferably, the media includes a well-tolerated fluid such as saline. The media may also include a substance that is radioactive in the active state.

In another embodiment, an outer balloon located on a distal end of the catheter has a coating of a media. The media is normally in an inactive state in which the media has no effect on tissue remodeling or proliferation and is transformable upon addition of energy to an active state in which the media affects tissue remodeling or proliferation. The catheter also includes a second lumen in fluid communication with the outer balloon at a distal end and fluidly connected to a source of fluid at a proximal end for expanding the outer balloon with the media so that the outer balloon is in contact with the tissue site, an inner balloon located on the distal end of the catheter and in close proximity to the outer balloon, and a third lumen in fluid communication with the inner balloon at a distal end. The third lumen is configured and dimensioned to receive a source of an activation factor at a proximal end for providing the energy needed to transform the media to the active state. The coating can be either on an outer surface of the outside balloon in contact with the tissue or an inner surface of the outside balloon. The coating may include bromide or iodide.

The present invention also relates to a method for controlling tissue remodeling or proliferation at a tissue site. The method includes the steps of fluidly connecting a quantity of cryo-medium to a catheter having at least two lumens; inserting the catheter into a patient and conveying it to the tissue site; dispensing the cryo-medium through a lumen having a plurality of holes at a distal end to deliver the cryo-medium to the tissue site; providing an inflatable balloon for securing the catheter to the site, the balloon having an outer impervious wall and an inner wall with holes therein; and conveying the cryo-medium between the outer and inner walls and in through the holes.

Preferably, the cryo-medium is maintained at a temperature below 14° C. In one embodiment, the cryo-medium is passed through an orifice to reduce the temperature of the cryo-medium. The catheter may have two spaced balloons, inflatable upstream and downstream of the tissue site. The catheter may also be provided with an inner passageway with a closed distal end and a peripheral wall with holes therein so that the cryo-medium may be dispensed through the holes.

BRIEF DESCRIPTION OF THE DRAWINGS

Preferred features of the present invention are disclosed in the accompanying drawings, wherein similar reference characters denote similar elements throughout the several views, and wherein:

FIG. 2 shows a longitudinal cross-sectional view through a first embodiment of catheter including two lumens.

FIG. 3 shows a further side view, partially in cross-section, of the embodiment illustrated in FIG. 2.

FIG. 4 shows a second embodiment of catheter including three lumens.

FIG. 5 shows a third embodiment of catheter including the use of four lumens.

DETAILED DESCRIPTION OF THE PREFERRED EMBODIMENTS

Figure 1:
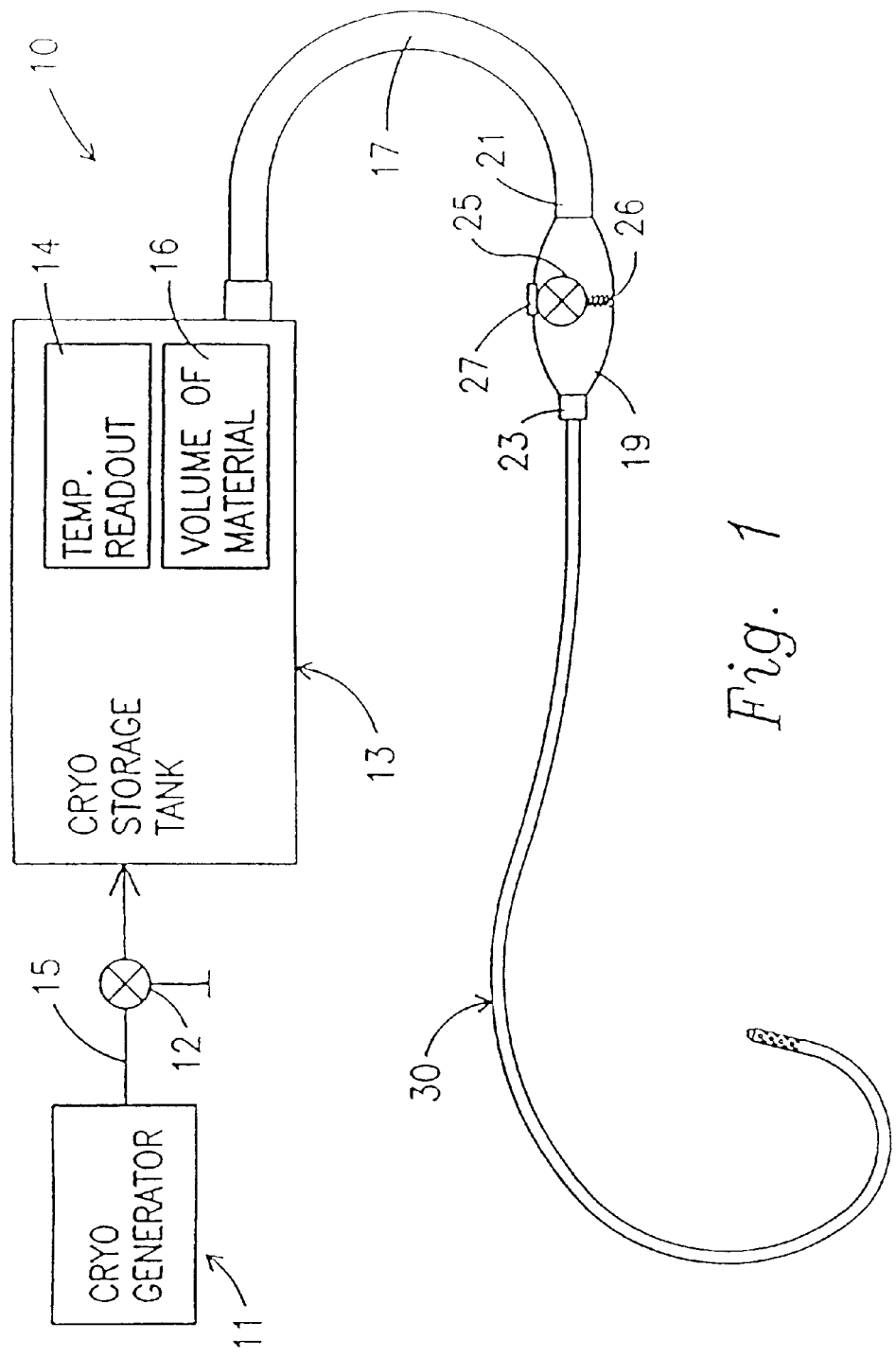
FIG. 1 shows a schematic representation of the overall system of the present invention.

FIG. 1 shows a first embodiment of the overall system 10 of the present invention. System 10 includes a cryo-generator 11, a cryo-storage tank 13, a conduit 15 interconnecting cryo-generator 11 with cryo-storage tank 13, and an outlet conduit 17 allowing flow of cryo-medium from storage tank 13 to a handheld controller 19 consisting of an inlet port 21, an outlet port 23, and a valve 25 having a valve actuator 27 that may be manipulated by the user to allow metering of a flow path through valve 25 to allow control of flow rate of cryo-medium into a catheter 30. Valve 25 may be of any desired type including one having a spring 26 biasing the valve head to a position of closure so that when actuator 27 is released, valve 25 is restored to the closed position. Any suitable valve that will firmly and repeatedly seat to block flow in the contemplated environment, i.e. that of a cryo-medium having a temperature between −10° C. and 4° C. maybe employed. A two-way valve which both delivers the cryo-medium through the catheter and creates a low pressure to withdraw the cryo-medium after the cooling function is completed can also be used. Such valves are well known to those skilled in the art.

As further seen in FIG. 1, storage tank 13 includes two gauges, a temperature readout gauge 14 and a volume or a pressure display 16. Volume display 16 may display rate of flow of cryo-medium in any manner well known to those skilled in the art. For example, the flow path of cryo-medium may include a conduit with a restricted orifice and with sensor lines just upstream and downstream of the restricted orifice. The pressure differential on either side of the restricted orifice relates to flow rate in a manner well known to those skilled in the art.

FIG. 2 shows more details of catheter 30. Catheter 30 includes two lumens: a first lumen 31 provided for insertion therethrough of a guide wire 33 designed to guide movement of catheter 30 to its desired location; and a second lumen 35 having a balloon 37 and a plurality of ports 39 in a prescribed pattern and extent designed to dispense cryo-medium to the desired location for the reasons explained herein. Catheter 30 also includes a hub 38 to which hand held controller 19 is connected.

FIGS. 3 and 4 show another embodiment of a catheter 40 according to the present invention having three lumens. A first lumen 41 includes a port 42 designed to allow insertion of a guide wire (not shown). A second lumen 43 is provided to allow inflation of a balloon 44. A third lumen 46 includes a plurality of holes 45 therein in a prescribed pattern and extent designed to allow dispensing of cryo-medium at the desired site.

With reference to FIG. 5, another embodiment of a catheter 50 includes all of the features of catheter 40 but with the addition of a further balloon 51 upstream of the site where cryo-medium is to be dispensed. Openings 53, corresponding to openings 45 of catheter 40, are provided in a prescribed pattern and extent and are located in an area between balloons 51 and 54. Thus, the area between balloons 51 and 54 define an isolated region therebetween where the cryo-medium is to be dispensed.

Figure 6:
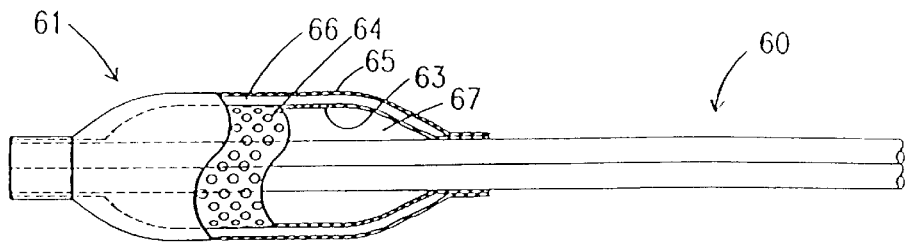
FIG. 6 shows a fourth embodiment of catheter including a two layered balloon having an inner layer with pores to deliver cryo-medium.

FIG. 6 shows a catheter 60 that includes a balloon 61 having an inner layer 63 and an outer layer 65, with inner layer 63 including openings 64 therethrough. The cryo-medium may be directed into a space 66 between inner layer 63 and outer layer 65 so that the cryo-medium may be dispensed within a chamber 67. In this embodiment, dispensing of the cryo-medium within chamber 67 eliminates direct contact between the cryo-medium and the tissue being treated. However, through heat exchange through inner layer 63 and outer layer 65 the effect is the same, namely, cooling of the tissues in a desired manner.

Figure 7:
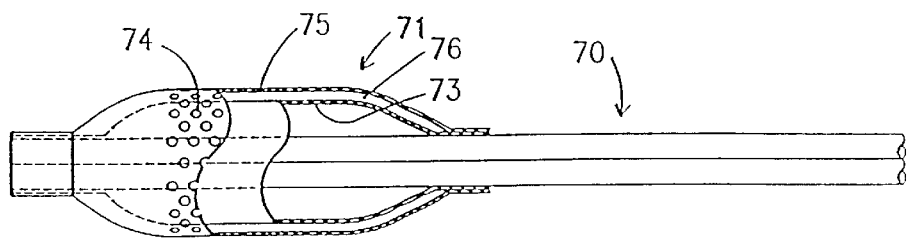
FIG. 7 shows a fifth embodiment of catheter having a two layered balloon with the outer layer having pores to deliver cryo-medium.

FIG. 7 shows a catheter 70 having a balloon 71 with an inner layer 73 and an outer layer 75. Openings 74 are formed in outer layer 75 and cryo-medium may be directed between layers 73 and 75 in a space 76 defined therebetween to allow cryo-medium to be dispensed therethrough. In this embodiment, as contrasted to catheter 60 illustrated in FIG. 6, the cryo-medium directly contacts the tissue being treated.

Figure 8:
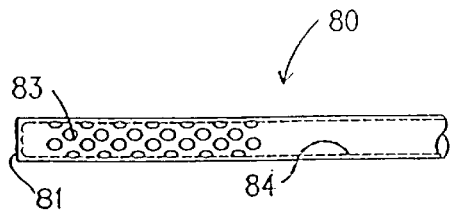
FIG. 8 shows a sixth embodiment of catheter devoid of a balloon but having a series of holes to deliver cryo-medium.
Figure 9:
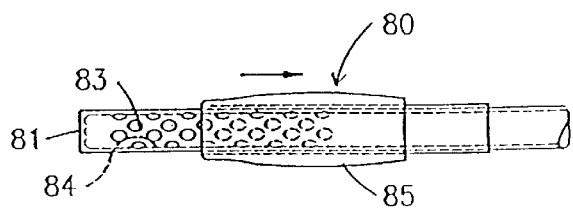
FIG. 9 shows the catheter of FIG. 8 with a flexible sheath covering the delivery holes, which sheath may be withdrawn to expose the holes and allow cryo-medium delivery.

FIG. 8 shows a catheter 80 that is devoid of a balloon but includes a distal end 81 that is closed. On the peripheral walls adjacent distal end 81 of catheter 80, a multiplicity of holes 83 are formed in a desired pattern and extent to allow dispensing of cryo-medium through an interior passageway 84 of catheter 80 and to the location of the desired site of application thereof. In FIG. 9, catheter 80 is seen to be provided with a flexible, resilient sheath 85 that covers openings 83 to preclude flow of cryo-medium. Catheter 80 can also include an additional lumen for a guide wire. Sheath 85 may be withdrawn from covering openings 83 in a manner well known to those skilled in the art to allow dispensing of cryo-medium, as desired.

As explained above, in order to fill storage tank 13 with cryo-medium, the cryo-generator comprises a compression chamber in which air is mixed with freon or helium and is compressed until the temperature falls between the range of 14° C. to −10° C. A combination of alcohol and dry ice, water, water mixed with saline, or water mixed with a suitable coolant can also be used instead of the air/freon/helium mixture. Thereafter, the cryo-medium is conveyed through conduit 15 by opening of valve 12 to storage tank 13. Storage tank 13 may be insulated in a manner well known to those skilled in the art to allow the temperature of the cryo-medium to be maintained substantially constant. The cryo-medium is conveyed in conduit 17 to handheld controller 19 which includes valve 25 and actuator 27. When the operator so desires, one of the catheters described above may be affixed to outlet port 23 of handheld controller 19 and the operator can operate actuator 27 to allow a variety of degrees of opening of valve 25 to allow flow of cryo-medium through the catheter to the desired location at the required temperature. Furthermore, any of the catheters may have a thermistor or similar temperature reading device located near the region in contact with the tissue and coupled to the temperature gauge so that the therapeutic temperature can be monitored.

If desired, the cryo-medium may be mixed with other substance or substances such as antibiotics, anticoagulants, antiproliferative agents, gene matter, etc. that may be disbursed at the desired site along with the cryo-medium intraluminally. These substance(s) may be mixed with the cryo-medium in cryo-generator 11, in storage tank 13, or downstream of handheld controller 19 within the catheter. These substances can also be delivered in the medium which is activated by cryo or can be separately delivered into the arterial wall after completion of the cryo-procedure.

Figure 10:
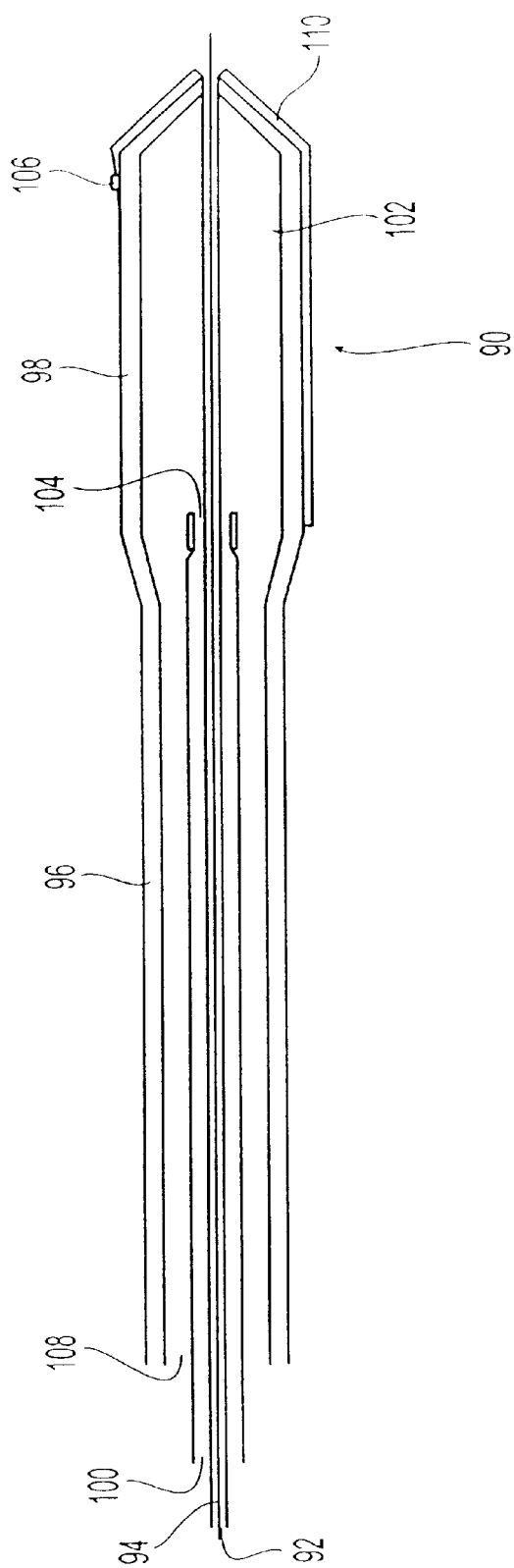
FIG. 10 shows another embodiment of a catheter according to the present invention.

FIG. 10 shows a catheter 90 that does not require the use of a compressor or other cryo-generator to achieve cryo-therapeutic temperatures. Catheter 90 has a first lumen 92 for insertion of a guide wire 94. As was the case for the other embodiments, guide wire 94 is directed to the desired location, usually under radiographic visualization, and catheter 90 is inserted in a patient over guide wire 94 through first lumen 92. Catheter 90 has a second lumen 96 which is in fluid communication with an outer balloon 98. Outer balloon 98 is inflated and expanded by the introduction of a fluid, preferably a liquid, into second lumen 96. When catheter 90 is inserted and outer balloon is inflated with a liquid, outer balloon 98 is in contact with the tissue to be treated. As will be described in more detail, it is the thermal properties of the liquid used to inflate outer balloon 98 that are utilized to cool the tissue at the application site.

Catheter 90 has a third lumen 100 which is in fluid communication with an inner balloon 102. A coolant gas is introduced into inner balloon 102 through third lumen 100. The coolant gas must pass through orifice 104 to enter inner balloon 102. The expansion of the coolant gas from third lumen 100 through orifice 104 and into inner balloon 102 produces a Joule-Thomson effect, i.e. an adiabatic expansion of the coolant gas resulting in a temperature reduction of the coolant gas. Thus, orifice 104 acts as a Joule-Thomson valve. Once in inner balloon 102, the coolant gas cools the liquid in outer balloon 98. The cooled liquid in turn cools the tissue in contact with outer balloon 98. Thus, the length of outer balloon 98 defines a so-called "freeze zone." In this regard, the tip of outer balloon 98 has a sensor 106 which monitors the temperature of the tissue. Several sensors can also be located along various lengths of outer balloon 98, inner balloon 102, or the body of catheter 90. When several sensors are used, a differential reading averaging the temperatures can be monitored or a single temperature which is the highest (or lowest) of all the measured temperatures can be monitored at different locations. The sensor(s) can also be used to monitor the inner tissue temperature before the cryo-procedure so that the temperature differential provides the treatment temperature.

Catheter 90 has a fourth lumen 108 which is also in fluid communication with inner balloon 102. Fourth lumen 108 is a coolant gas removal conduit that removes the coolant gas from inner balloon 102 at such a rate to control the rate and degree of cooling of the liquid in outer balloon 98. Fourth lumen 108 can be connected to a vacuum to assist in removing the coolant gas from inner balloon 102 and further control the rate of removal of the coolant gas. Continuously withdrawing the coolant gas through a vacuum creates an active vacuum insulation surrounding the liquid. Furthermore, fourth lumen 108 can be connected to third lumen 100 so that a closed loop cycle for recovery and reuse of the coolant gas is formed.

In operation, by using orifice 104 as a Joule-Thomson valve, the coolant gas in inner balloon 102 cools the liquid in outer balloon 98. The liquid, in turn, cools the tissue in contact with outer balloon 98. A number of different treatment effects can be achieved with catheter 90. For example, by varying the rate of addition and removal of the coolant gas from third and fourth lumens 100, 108, cycles of cooling and thawing of tissue can be created to cause selective cell death. Another way to achieve cycles of cooling and thawing is to repeat the cryotherapeutic procedure multiple times until the desired effect on the tissue is achieved. One liquid that it particularly suitable for use with catheter 90 is saline. Saline is well tolerated by the body and has desirable thermal properties. However, a wide variety of liquids, each having their own thermal characteristics, can be used in catheter 90. The liquid used to expand outer balloon 98 should be selected based on a number of factors including the particular tissue being treated, the anatomical region of the tissue, the desired treatment on the tissue, and the coolant gas used. Similarly, the coolant gas can be selected based on analogous factors. In this regard, R-410 available from Allied Signal Inc. (Morristown, N.J.) has been shown to be a suitable coolant capable of reaching a temperature of −50° C. after expansion through orifice 104.

Neither third and fourth lumens 100, 108 nor outer and inner balloons 98, 102 need have a circular cross section. The shape can be chosen to create a freeze zone of a desired shape and size. Furthermore, the diameter of outer and inner balloons 98, 102 as well as the temperature of the coolant gas can be tailored to the tissue that is being treated. For example, a depth of penetration (ie. the radial distance from catheter 90 of the freeze zone) of 1 mm to 2 mm is typically needed to treat vascular tissue with small vessels. As the size of the vessel increases, a greater depth of penetration is needed and can be obtained by varying the size of the balloons 98, 102, the coolant gas, the liquid in outer balloon 98, and/or the geometry of orifice 104.

In an alternative embodiment of catheter 90, outer balloon 98 is expanded with a media that has two states: an inactive state in which the media is biologically inert and has no effect on tissue proliferation or modeling, and an active state in which the media is biologically active to control tissue proliferation and modeling. The media is ordinarily in the inactive state. In order for the media to go into the active state, some type of activation factor has to induce the transformation from the inactive state to the active state. In this alternative embodiment of catheter 90, the activation factor is present in inner balloon 102 and introduction of the activation factor in inner balloon 102 while the media is in outer balloon 98 is sufficient to induce the transformation into the active state. When the media is in the active state, the media can cause cell death in the tissue near outer balloon 98.

A number of different media having inactive and active states and activation factors are known to those of ordinary skill in the art and can be used with catheter 90. Specifically, there are substance that are non-radioactive until energy in the form of heat or light are added. Examples of such substances include bromide or iodide solutions or beads. After the addition of energy, the substances begin to exhibit radiation. For example, outer balloon 98 can contain saline mixed with one of these substances and inner balloon 102 can transports the energy. Once the energy comes in contact with outer balloon 98, radiation is emitted to the surrounding tissue to control tissue proliferation and modeling. The delivery of energy in the form of light can be accomplished with an optical fiber that is exposed to outer balloon 98. As the light source does not have to emit visible light, the light source can be a x-ray source, a beta radiation source, or gamma radiation source.

In another alternative embodiment of catheter 90, outer balloon 98 is coated with the media which is in its inactive state. The coating (shown as optional coating 110 in FIG. 10) can be either on the outside surface of outer balloon 98 in direct contact with the tissue, or on the inside surface of outer balloon 98. Upon introduction of the activation factor, the media is transformed into its active state. Outer balloon 98 can also be coated with a synthetic or biological pharmaceutical agent which remains inactive on the outside balloon surface or the inside balloon surface until activation of the agent induces release of a biologically active substance such as a singlet oxygen or other radical ions. The family of porphyrins, which includes lutetium-texaphyrin, protoporphyrin-9, and gadolinium-texaphyrin, or similar molecules that release electrons when activated by light is particularly effective in the treatment of atherosclerosis.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A catheter for controlling tissue remodeling or proliferation at a tissue site comprising:

an outer balloon located on a distal end of the catheter;

a first lumen in fluid communication with the outer balloon at a distal end and fluidly connected to a source of liquid at a proximal end for expanding the outer balloon with liquid to contact the tissue site;

a second lumen fluidly connected to a source of coolant fluid at a proximal end for transporting the coolant fluid to a distal end of the second lumen to cool the liquid in the outer balloon and thereby the tissue site to a cryo-therapeutic temperature; and an inner balloon in fluid communication with the distal end of the second lumen in close proximity to the outer balloon;

a third lumen surrounding at least a portion of the second lumen and in fluid communication with the inner balloon for removing the coolant fluid from the inner balloon;

wherein the second lumen includes an orifice configured and dimensioned to allow the coolant fluid to expand as it passes therethrough to reduce coolant fluid temperature; and the fluid communication between the second lumen and the inner balloon is through the orifice to allow the coolant fluid to expand into the inner balloon.

2. The catheter of claim 1 further comprising a fourth lumen configured and dimensioned to receive a guide wire for directing the catheter to the tissue site.

3. The catheter of claim 2 wherein the third lumen is fluidly connected to a vacuum to assist in removing the coolant fluid from the inner balloon.

4. The catheter of claim 1 wherein the outer balloon has a temperature sensor for monitoring the temperature of the tissue site.

5. The catheter of claim 1 further comprising a valve between the fluid coolant source and the second lumen for controlling introduction of the coolant gas into the second lumen.

6. The catheter of claim 1 wherein the coolant fluid temperature is sufficient to freeze the liquid after expansion through the orifice.

7. A catheter for controlling tissue remolding or proliferation at a tissue site comprising:

a first lumen configured and dimensioned to receive a guide wire for directing the catheter to the tissue site;

an outer balloon located on a distal end of the catheter;

a second lumen in fluid communication with the outer balloon at a distal end and fluidly connected to receive a media at a proximal end for expanding the outer balloon with the media so that the outer balloon is in contact with the tissue site, the media normally in an inactive state in which the media has no effect on tissue remodeling or proliferation and the media transformable upon addition of energy to an active state in which the media effects tissue remodeling or proliferation;

an inner balloon located on the distal end of the catheter and in close proximity to the outer balloon; and a third lumen in fluid communication with the inner balloon at a distal end for receiving an activation factor at a proximal end and transporting the activation factor to the inner balloon to provide the energy needed to transform the media to the active state.

8. The catheter of claim 7 wherein the activation factor is light or heat.

9. The catheter of claim 7 wherein the media includes saline.

10. The catheter of claim 7 wherein the media includes a substance that is radioactive in the active state.

11. A method for controlling tissue remodeling or proliferation at a tissue site including the steps of:

fluidly connecting a quantity of cryo-medium to a catheter having at least two lumens;

inserting said catheter into a patient and conveying said catheter to said tissue site;

dispensing the cryo-medium through a lumen within said catheter, the lumen having a plurality of holes at a distal end to deliver the cryo-medium to the tissue site;

providing an inflatable balloon for securing the catheter to the site, the balloon having an outer impervious wall and an inner wall with holes therein; and conveying the cryo-medium between the outer and inner walls and in through the holes.

12. The method of claim 11 wherein said providing step includes the step of maintaining said cryo-medium at a temperature below 14° C.

13. The method of claim 11 wherein said fluidly connecting step includes the step of passing the cryo-medium through an orifice to reduce the temperature of the cryo-medium.

14. The method of claim 11 wherein said catheter has two spaced balloons, inflatable upstream and downstream of said tissue site.

15. The method of claim 11 wherein said catheter has an inner passageway with a closed distal end and a peripheral wall with holes therein, said method including the step of dispensing the cryo-medium through said holes.

16. A catheter for controlling tissue remodeling or proliferation at a tissue site comprising:

a first lumen configured and dimensioned to receive a guide wire for directing the catheter to the tissue site;

an outer balloon located on a distal end of the catheter and having a coating of a media, the media normally in an inactive state in which the media has no effect on tissue remodeling or proliferation and the media transformable upon addition of energy to an active state in which the media effects tissue remodeling or proliferation;

a second lumen in fluid communication with the outer balloon at a distal end and fluidly connected to a source of fluid at a proximal end for expanding the outer balloon with the media so that the outer balloon is in contact with the tissue site;

an inner balloon located on the distal end of the catheter and in close proximity to the outer balloon; and a third lumen fluid communication with the inner balloon at a distal end and configured and dimensioned to receive an activation factor at a proximal end for providing the energy needed to transform the media to the active state.

17. The catheter of claim 16 wherein the coating is on an outer surface of the outside balloon.

18. The catheter of claim 17 wherein the coating includes bromide or iodide.

19. The catheter of claim 17 wherein the coating includes a radioactive material.

* * * * *